United States Patent [19]

Böger et al.

[11] 4,228,175
[45] Oct. 14, 1980

[54] BIS-(PHENOXYALKYL-2-IMIDAZOLIN)-1,1-SULFIDES, PROCESS FOR THEIR MANUFACTURE, COMPOSITIONS WHICH CONTAIN THESE SULFIDES AS ACTIVE COMPONENT AND USE THEREOF IN PEST CONTROL

[75] Inventors: Manfred Böger, Rhein, Fed. Rep. of Germany; Josef Drabek, Oberwil, Switzerland; Günter Mattern, Liestal, Switzerland; Water Traber, Reinach, Switzerland

[73] Assignee: Ciba-Geigy Corporation, Ardsley, N.Y.

[21] Appl. No.: 69,033

[22] Filed: Aug. 23, 1979

[30] Foreign Application Priority Data

Aug. 28, 1978 [CH] Switzerland ............... 9079/78
Aug. 10, 1979 [CH] Switzerland ............... 7370/79

[51] Int. Cl.² ............... A61K 31/415; C07D 233/22
[52] U.S. Cl. ............... 424/273 R; 548/349
[58] Field of Search ............... 548/349; 424/273 R

[56] References Cited

PUBLICATIONS

Buechi et al. "Chem. Abstracts", vol. 84 (1976) No. P150,800J.

Primary Examiner—Alan L. Rotman
Assistant Examiner—R. W. Ramsuer
Attorney, Agent, or Firm—John J. Maitner

[57] ABSTRACT

Compound of the formula I

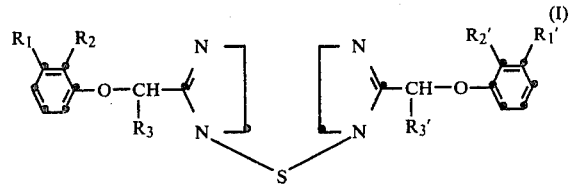

wherein $R_1$, $R_1'$, $R_2$ and $R_2'$ are each chlorine or methyl and $R_3$ and $R_3'$ are each hydrogen or $C_1$—$C_4$-alkyl possess valuable pesticidal in particular acaricidal properties.

8 Claims, No Drawings

BIS-(PHENOXYALKYL-2-IMIDAZOLIN)-1,1-SULFIDES, PROCESS FOR THEIR MANUFACTURE, COMPOSITIONS WHICH CONTAIN THESE SULFIDES AS ACTIVE COMPONENT AND USE THEREOF IN PEST CONTROL

The present invention relates to novel bis-(phenoxyalkyl-2-imidazoline)-1,1'-sulfides which are effective against pests, a process for their manufacture, compositions which contain these sulfides as active component and a method of controlling pests which comprises the use of the novel compounds.

2-(Phenoxyalkyl)-2-imidazoline derivatives which possess pesticidal, in particular ectoparasticidal, action, are known (cf. for example South African patent application No. 78/2449, Japanese published patent specification No. 76/106739, German Offenlegungsschrift No. 2 756 638 and 2 756 639). The present invention provides novel compounds of this type which also possess an action against pests, in particular against representatives of the order Acarina, and which are particularly suitable for practical use on account of their advantageous biological properties.

The novel bis-(phenoxyalkyl-2-imidazoline)-1,1'-sulfides have the formula I

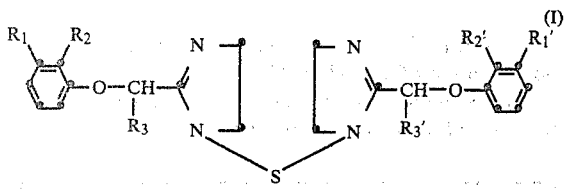

wherein $R_1$, $R_1'$, $R_2$ and $R_2'$, each independently of the other, are chlorine or methyl, and $R_3$ and $R_3'$, each independently of the other, are hydrogen or $C_1$–$C_4$-alkyl.

Possible alkyl groups $R_3$ and $R_3'$ are methyl, ethyl, n-propyl, isopropyl, n-butyl, isobutyl, sec-butyl and tert-butyl.

Preferred substituents and combinations thereof in compounds of the formula I are:

(1) for $R_1$, $R_1'$, $R_2$ and $R_2'$: simultaneously methyl or chlorine;

(2) for $R_3$ and $R_3'$: simultaneously hydrogen or ethyl, preferably ethyl.

The compounds of formula I exist in the form of acid addition salts, e.g. mineral salts, and can be employed in the form of their salts. Accordingly, the present invention is to be construed as comprising both the free compounds and the acid addition salts thereof.

Surprisingly, it has been found that the compounds of the formula I are very effective against both plant-destructive acarids (mites, e.g. of the families Tetranychidae, Tarsonemidae, Eriophydae, and Glycyphagidae) and against ectoparasitic acarids (mites and ticks, e.g. of the families Ixodidae, Argasidae, Sarcoptidae and Dermanyssidae) that are harmful to productive livestock. Furthermore, it has also been found that these acaricidal properties are allied to a low toxicity to warm-blooded animals, which makes the compounds of the formula I and their non-toxic acid addition salts particularly suitable for controlling pests of the order Acarina in crops of useful plants and ornamentals, chiefly in the field of fruit and citrus fruit growing, and also for controlling ectoparasitic ticks and mites in productive livestock.

The compounds of the formula I are obtained by methods analogous to known ones, e.g. by reacting a compound of the formula II

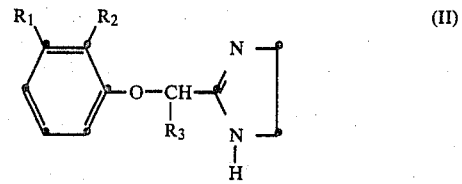

in the presence of a base, with a compound of the formula III

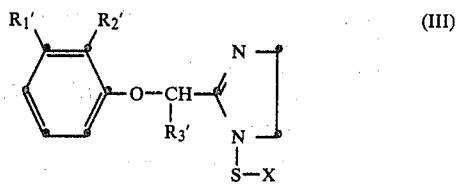

in which formulae II and III above $R_1$, $R_1'$, $R_2$, $R_2'$, $R_3$ and $R_3'$ are as defined for formula I and X is a halogen atom, in particular a chlorine or bromine atom.

The process is advantageously carried out at a temperature between $-20°$ and $+30°$ C., under normal or slightly elevated pressure, and preferably in the presence of a solvent or diluent which is inert to the reactants.

Examples of suitable solvents or diluents are ethers and ethereal compounds, such as diethyl ether, diisopropyl ether, dioxane and tetrahydrofurane; aromatic hydrocarbons, such as benzene, toluene and xylenes; ketones, such as acetone, methyl ethyl ketone and cyclohexanone.

Suitable bases for this process are in particular tertiary amines, such as trialkylamines, pyridines and dialkyl anilines, and hydroxides, oxides, carbonates and bicarbonates of alkali metals and alkaline earth metals, and also alkali metal alcoholates, e.g. potassium tert-butylate and sodium methylate.

The compounds of formula I so obtained can be converted into their acid salts by methods which are known per se.

The compounds of formula I, wherein $R_3$ and/or $R_3'$ are alkyl, exist in the form of optically active isomers. Accordingly, racemic mixtures are obtained if no optically active starting materials are employed in the manufacture of these compounds. Such mixtures of isomers can be separated into the individual isomers, e.g. by chromatographic separating methods. The invention is to be construed as comprising both the individual optically active isomers and mixtures thereof.

The starting materials employed in the above process are known (cf. South African patent application No. 76/2449 and German Offenlegungsschrift No. 2 756 638) or they can be obtained by methods analogous to known ones.

The compounds of formula I are employed in this invention as pure active substance or they form a constituent of compositions which additionally contain suitable carriers or adjuvants or mixtures thereof.

Suitable carriers and adjuvants can be solid or liquid and correspond to the substances conventionally used in the art of formulation, e.g. natural or regenerated substances, solvents, dispersing agents, wetting agents, tackifiers, thickeners binders and/or fertilisers.

The acaricidal action of the compositions of the invention can be substantially broadened by addition of other acaricides and/or insecticides. Examples of suitable additives are: organophosphorus compounds, nitrophenols and derivatives thereof, formamidines, ureas, pyrethroids, carbamates, and chlorinated hydrocarbons.

The compositions of the invention can be formulated e.g. as dusts, granulates, dispersions, solutions and suspensions, and also as water-dispersible wettable powders, pastes, emulsions and emulsifiable concentrates. The content of active substance (compound of formula I) in the above compositions is between 0.1 and 95%, though higher concentrations can also be used if the compositions are applied from an aircraft or other appropriate application device.

The active substances of the formula I can be formulated e.g. as follows (throughout this specification, the parts are by weight):

Emulsifiable concentrate I 20 parts of active substance of the formula I are dissolved in 70 parts of xylene, and to this solution are added 10 parts of an emulsifying agent consisting of a mixture of an arylphenylpolyglycol ether and the calcium salt of dodecylbenzenesulfonic acid. The resultant emulsifiable concentrate can be diluted with water in any ratio to form a milky emulsion.

Emulsifiable concentrate II

With stirring, 5 to at most 30 parts of active substance are dissolved at room temperature in 30 parts of dibutyl phthalate, 10 parts of Solvent 200 (low viscosity, highly aromatic petroleum distillate) and 15 to 35 parts of Dutrex 238 FC (viscous highly aromatic petroleum distillate). To this solution are added 10 parts of an emsulfier mixture consisting of caster oil polyglycol ether and the calcium salt of dodecylbenzenesulfonate. The resultant emulsifiable concentrate forms milky emulsions in water.

Wettable powder

The following ingredients are intensively mixed in a mixing apparatus: 5 to 30 parts of active substance, 5 parts of an absorbent carrier (silica gel K 320 or Wessalon S), 55 to 80 parts by weight of a carrier (Bolus alba or kaolin B 24) and a dispersing agent mixture consisting of 5 parts of a sodium laurylsulfonate and 5 parts of an alkylaryl polyglycol ether. This mixture is ground to a granular size of 5–15 μm in a disc attrition mill or air jet mill. The resultant wettable powder forms a good suspension in water.

Dust 5 parts of finely ground of active substance are intensively mixed with 2 parts of precipitated silicic acid and 93 parts of talcum.

Pour-on solution

A 100 ml pour-on solution is obtained as follows: With stirring, 30.0 g of active substance are dissolved in 48.0 g of benzyl alcohol, if necessary while heating gently. Then 3.0 g of sodium dioctylsulfosuccinate and 19.8 g of ground nut oil are added to the above solution and dissolved by heating and thorough stirring.

The invention is illustrated in more detail by the following Examples.

EXAMPLE 1

Manufacture of bis-(2,3-dimethylphenoxymethyl)-2-imidazoline)-1,1'-sulfide 11 g of triethylamine are added slowly dropwise at 0° C. to a solution of 20.4 g of 2-(2,3-dimethylphenoxymethyl)-2-imidazoline in 200 ml of methylene chloride, followed by the slow dropwise addition of 5.15 g of freshly distilled sulfur chloride. The reaction mixture is then stirred for about 2 hours in an ice bath, the resultant solution is diluted with water and the organic phase is washed repeatedly with water, dried over sodium sulfate and concentrated completely. The residue is stirred in hexane and recrystallisation of the solid precipitate yields bis-(2,3-dimethylphenoxymethyl)-2-imidazoline)-1,1'-sulfide (compound 1) of the formula

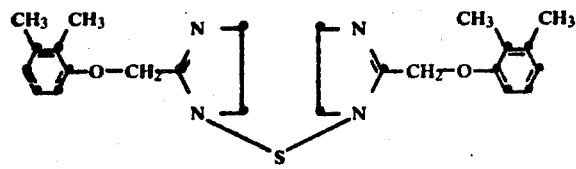

in the form of a light beige-coloured powder with a melting point of 112°–114° C.

The following compounds of the formula I can also be obtained in analogous manner:

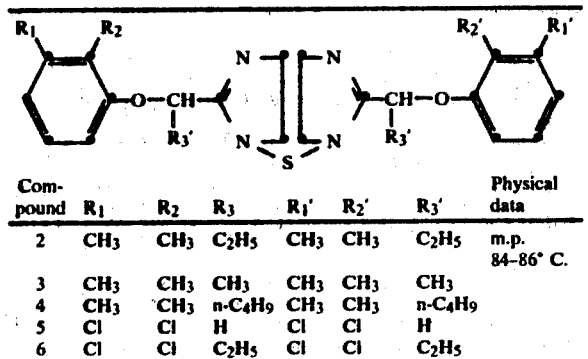

| Compound | $R_1$ | $R_2$ | $R_3$ | $R_1'$ | $R_2'$ | $R_3'$ | Physical data |
|---|---|---|---|---|---|---|---|
| 2 | $CH_3$ | $CH_3$ | $C_2H_5$ | $CH_3$ | $CH_3$ | $C_2H_5$ | m.p. 84–86° C. |
| 3 | $CH_3$ | $CH_3$ | $CH_3$ | $CH_3$ | $CH_3$ | $CH_3$ | |
| 4 | $CH_3$ | $CH_3$ | $n-C_4H_9$ | $CH_3$ | $CH_3$ | $n-C_4H_9$ | |
| 5 | Cl | Cl | H | Cl | Cl | H | |
| 6 | Cl | Cl | $C_2H_5$ | Cl | Cl | $C_2H_5$ | |

EXAMPLE 2

Action against plant-destructive acarids (mites) *Tetranychus urticae* (OP-sensitive) and *Tetranychus cinnabarius* (OP-tolerant)

The primary leaves of *Phaseolus vulgaris* plants were infected with a infested piece of leaf from a mass culture of *Tetranychus urticae* (OP-sensitive) or *Tetranychus cinnabarius* (OP-tolerant). (The tolerance refers to the tolerance of diazinone). The treated, infested plants were sprayed dripping wet with a test solution containing 400 or 200 ppm of the compound to be tested. The number of living and dead imagines and larvae (all mobile stages) was evaluated under a stereoscopic microscope after 24 hours and again after 7 days. One plant was used for each test substance and test species. During the test run, the plants stood in greenhouse compartments at 25° C.

In the above test, the compounds of formula I were effective against adults and larvae of the species *Tetranychus urticae* and *Tetranychus cinnabarius*.

EXAMPLE 3

Action against ectoparasitic acarids (ticks: *Rhipicephalus bursa* (imagines and larvae), *Amblyomma hebraeum* (♀ imagines, nymphs and larvae) and *Boophilus microplus* (larvae, OP-sensitive and OP-tolerant)

The test organisms employed were about 50 larvae, about 25 nymphs or about 10 imagines of each of the tick species *Rhipicephalus bursa*, *Amblyomma hebraeum* and *Boophilus microplus*. The test organisms were immersed briefly in an aqueous emulsion or solution containing 0.1, 1.0, 10, 50 or 100 ppm of the respective compound. The emulsions or solutions in test tubes were then absorbed by cotton wool and the wetted test organisms were kept in the contaminated tubes. Evaluation of mortality at each concentration was made after 3 days (larvae) and 14 days (nymphs and imagines).

Compounds of the formula I were effective in this test against larvae, nymphs and imagines of *Rhipicephalus bursa* and *Amblyomma hebraeum* and against larvae (OP-resistant and OP-sensitive) of *Boophilus microplus*.

What is claimed is:

1. A compound of the formula I

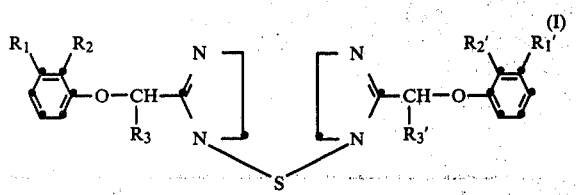

wherein $R_1$, $R_1'$, $R_2$ and $R_2'$ are, each independently of the other, chlorine or methyl and $R_3$ and $R_3'$ are, each independently of the other, hydrogen or $C_1$-$C_4$-alkyl and the acid addition salts thereof.

2. A compound as claimed in claim 1 wherein $R_1$, $R_1'$, $R_2$ and $R_2'$ are the same and are chlorine or methyl.

3. A compound as claimed in claim 1 or 2 wherein $R_3$ and $R_3'$ are the same and are hydrogen or ethyl.

4. A compound as claimed in claim 1 of the formula

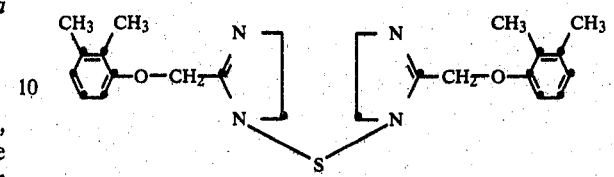

5. A compound as claimed in claim 1 of the formula

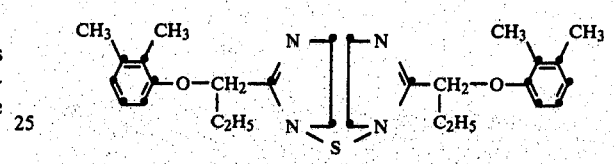

6. An acaricidal composition comprising an acaricidally effective amount of a compound as claimed in claim 1, together with an inert, solid or liquid diluent or carrier therefor.

7. A method of controlling acarids at a locus which method comprises applying to said locus an acaricidally effective amount of a compound as claimed in claim 1.

8. A method as claimed in claim 7 wherein the acarids are acarids which cause damage to plants and the locus comprises an agricultural or horticultural crop.

* * * * *